(12) United States Patent
Karpman et al.

(10) Patent No.: US 6,214,012 B1
(45) Date of Patent: Apr. 10, 2001

(54) METHOD AND APPARATUS FOR DELIVERING MATERIAL TO A DESIRED LOCATION

(75) Inventors: Robert R. Karpman; Thomas M. Hansen, both of Phoenix; Anna G. U. Brantley, Tempe, all of AZ (US)

(73) Assignee: Harrington Arthritis Research Center, Phoenix, AZ (US)

( * ) Notice: Subject to any disclaimer, the term of this patent is extended or adjusted under 35 U.S.C. 154(b) by 0 days.

(21) Appl. No.: 09/191,915

(22) Filed: Nov. 13, 1998

(51) Int. Cl.$^7$ ................................................. A61B 17/58
(52) U.S. Cl. ................................ 606/93; 606/61; 606/71; 606/73; 606/92
(58) Field of Search .................... 606/73, 71, 92, 606/93, 95; 604/890.1, 285, 264, 271; 128/898

(56) References Cited

U.S. PATENT DOCUMENTS

| | | |
|---|---|---|
| 4,653,489 | 3/1987 | Tronzo . |
| 4,772,261 * | 9/1988 | Van Hoff et al. ................. 604/51 |
| 4,787,882 * | 11/1988 | Claren ........................... 604/264 |
| 5,047,030 | 9/1991 | Draenert ......................... 606/65 |
| 5,800,407 * | 9/1998 | Eldor ............................ 604/264 |
| 5,871,484 * | 2/1999 | Spievack et al. ................ 606/72 |

FOREIGN PATENT DOCUMENTS

| | | |
|---|---|---|
| 0 490 417 A1 | 6/1992 | (EP) . |
| 07051292 | 2/1995 | (EP) . |
| 07222752 | 8/1995 | (EP) . |

OTHER PUBLICATIONS

Database WPI, Derwent Publications, Ltd., Aug. 11, 1998, Week 9842.
Campbell's Operative Orthapaedics, pp. 512–532 (undated).
Lawyer's Medical Cyclopedia, pp. 380–385; 406–407 (undated).
Orthopedic Surgery, pp. 319–321 (undated).
Medical Dictionary (unidentified) pp. 468–469 (undated).

* cited by examiner

*Primary Examiner*—Henry J. Recla
*Assistant Examiner*—Julian W. Woo
(74) *Attorney, Agent, or Firm*—Snell & Wilmer, LLP

(57) ABSTRACT

A method and apparatus for the effective delivery of a material, such as cement, to a desired location in a human. In one embodiment of the invention, a bone screw, including a head portion, a cannulated slotted shaft portion and a tip portion, includes an injection site for removably attaching an injection device, such as a syringe. Since the shaft portion is slotted, injected material flows from the cannulated shaft and is able to exit into surrounding tissue through the slot in the shaft.

34 Claims, 14 Drawing Sheets

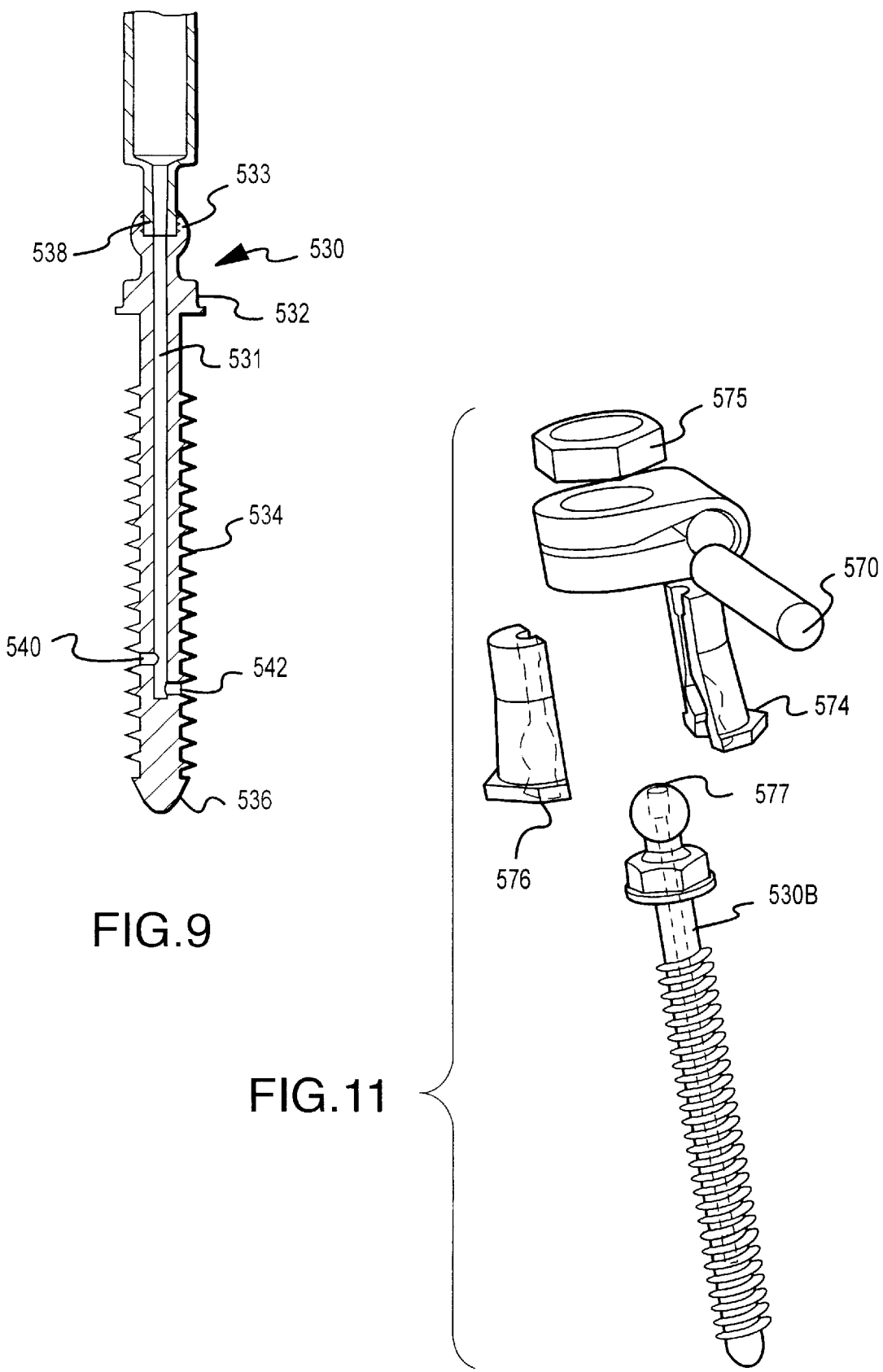

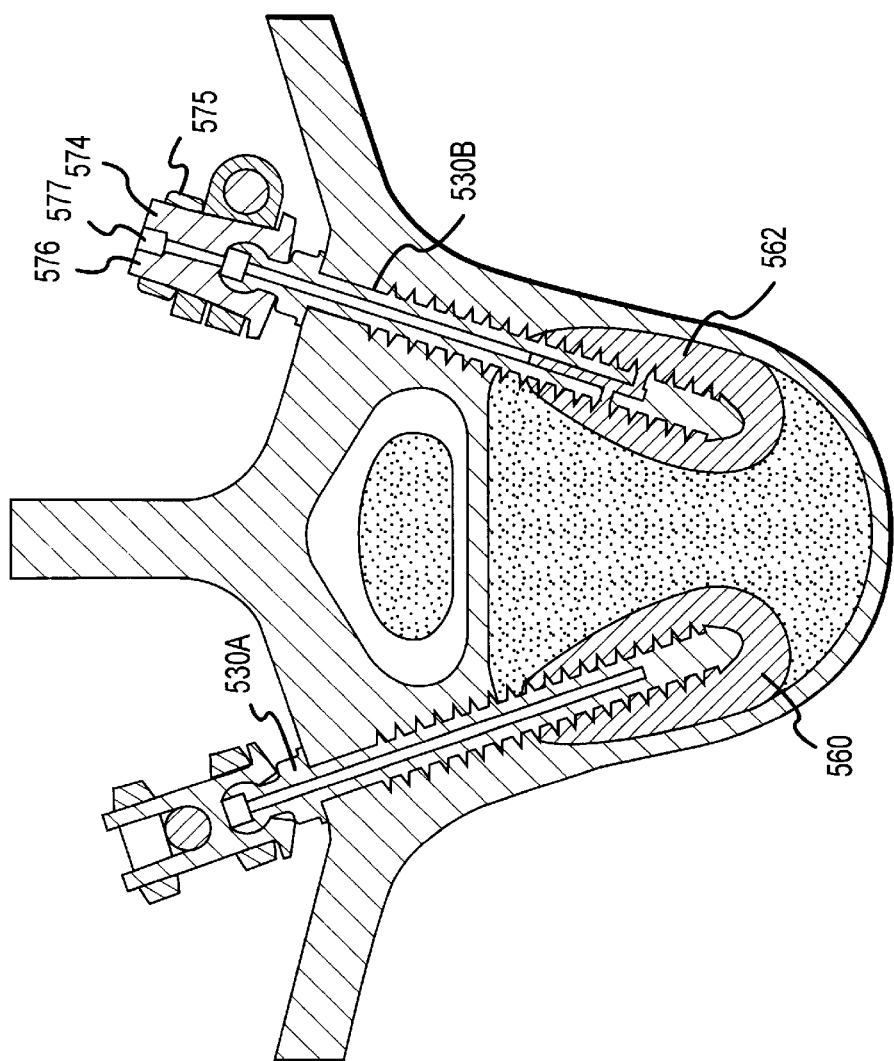

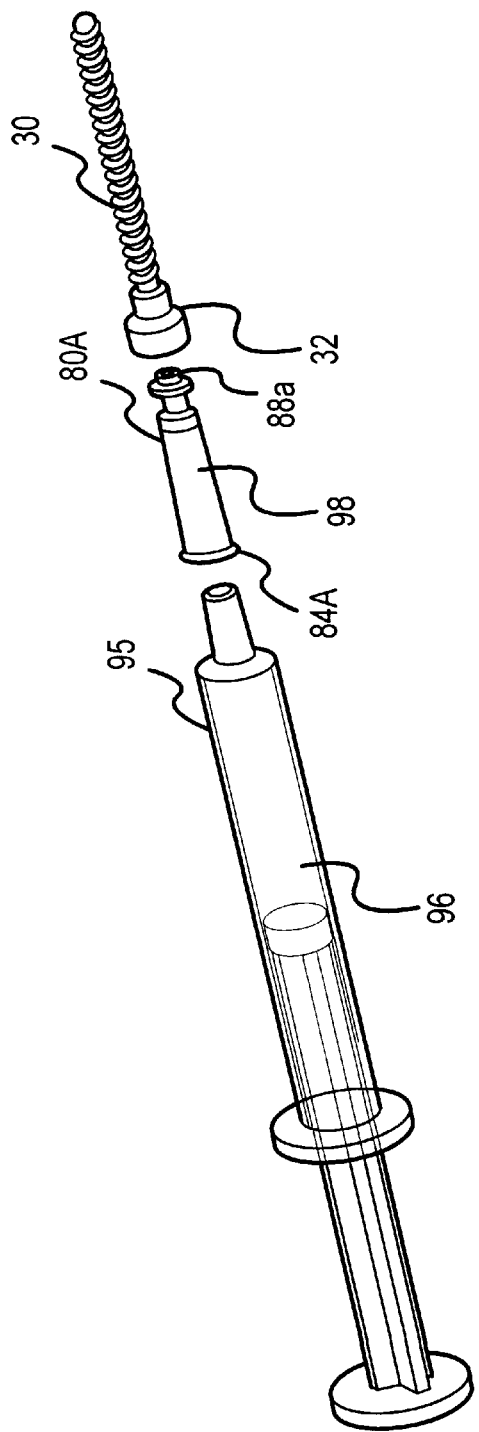
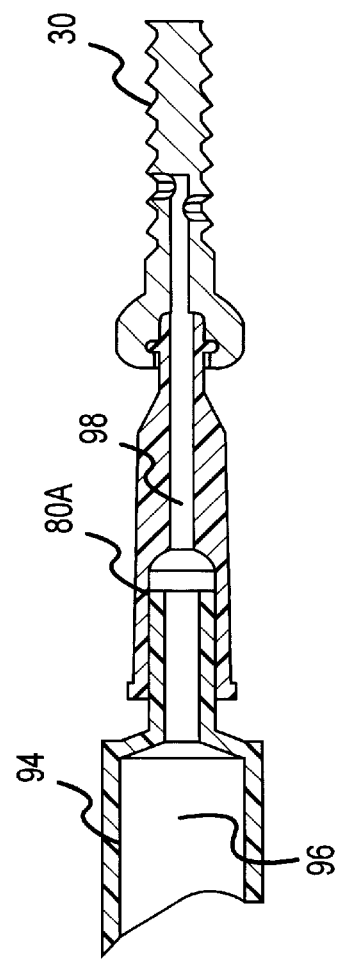
FIG. 15
FIG. 15A

METHOD AND APPARATUS FOR DELIVERING MATERIAL TO A DESIRED LOCATION

TECHNICAL FIELD

The present invention generally relates to a method and apparatus for delivering material to a desired location through use of a slotted delivery device and, more particularly, to a bone screw which is configured for delivery of an injectable material into a bone.

BACKGROUND

In a number of medical procedures it becomes necessary to deliver material to a desired location. For example, in connection with many cancer treatments, particularly treatments to bones inflicted with cancer cells, it is desirable to deliver materials, usually in injectable form, to particular locations within the bone. In other instances, particularly when use of bone screws is desirable, materials, also usually of an injectable form, often need to be delivered to aid in fixation of the screw.

In the context of the present invention, as will be discussed in greater detail hereinbelow, the present inventors have discovered methods and apparatus which offer advantages over currently known methods and apparatus useful in the administration of such materials. For convenience of explanation and illustration, the present invention will be described in conjunction with various applications, but principally, bone screw and drug or other medication delivery systems. It should be appreciated, however, that various other applications and embodiments will be apparent in light of the following disclosure.

In the context of bone screws, as is known, bone screws may be attached to bones for any number of reasons, but generally such screws are attached for the purpose of repair of the weakened bone structure to support bones or bone structure which have become broken or weakened. In many cases, the brake or weakening of the bone is in whole, or at least in part, due to disease. That is, the bone breaks or weakens as a result of disease, e.g., osteoporosis. Current techniques, in general, do not take into consideration that condition in the context of the repair. Stated another way, the technique used to repair bone often fails to address the situation under which the bone broke or weakened in the first place.

For example, in accordance with conventional methods of attaching bone screws to bones, bone cement (typically an acrylic resin material) is injected through a pilot hole drilled into the bone prior to inserting the bone screw. After the bone screw is inserted into the site, the bone cement theoretically hardens to strengthen the fixation site. This method, however, lacks control over the location or amount of bone cement applied. For example, it is often difficult to control the placement of adhesive near tissue regions, specifically in the spinal cord region, and improper placement can result in injury. Moreover, too little bone cement or improper placement of the bone cement may result in a weak fixation site, which may lead to undesirable extraction of the bone screw from the fixation site. For example, if the bone has been broken due to, in whole or in part, a medical condition, the use of cement in this fashion may not materially enhance fixation. Specifically, if the bone is weakened due to, for example, osteoporosis, then merely adding an adhesive to the area, particularly if applied in a weakened area, may not address the pre-existing condition.

Moreover, in some cases use of the adhesive in this conventional manner can result in even more deleterious effects. Consider, for example, the case in which the adhesive begins to cure before, or during the insertion of the screw. In such a case, instead of enhancing the fixation of the screw, the adhesive may actually bind to the distal end of the screw, and, as the screw is inserted, cause further damage to the already weakened bone. Such effects, of course, may not be immediately detectable. That is, in some cases, while an initial "fix" may be obtained, the overall weakening of the fixation site may result in a weakening of the attachment over time, or in the best of cases, simply not aid in securing long term fixation.

Various bone screw configurations are known. For example, cannulated screws are known and typically used for such conventional applications. Alternatively, such cannulated screws are also utilized in connection with various pressurizing techniques. In connection with these techniques, suction is used to suck (i.e., withdraw) the blood and fat out of the bone canal. For example, in U.S. Pat. No. 5,047,030 issued Sep. 10, 1991 to Draevert, a suction drainage bone screw is described. The screw described is used initially to withdraw the blood and fat from a region surrounding the screw, such as by use of suctioning. While described as an advantage over existing pressurizing techniques, in all of the disclosed embodiments the removal of material is an important, if not essential aspect of the screw's success.

As described in the '030 patent, the bone screw is used to suck blood, fat and bone marrow out of the bone canal and its vicinity for suction drainage in the application of bone cement. Specifically, as described in the '030 patent, a cannulated bone screw is anterolaterally inserted into a distal tip of the prosthesis into a cortico-spongious plug, to ensure that the distal and proxible medullary canal remain delimited from the screw by means of the filter. The bone is then filled with bone cement, mixed under vacuum but pre-compressed prior to introduction to the bone, i.e., femur. In accordance with the disclosed embodiment, the bone cement is sucked deep down into the femur by the vacuum applied via the distal cannulated bone screw. Once a prosthesis component is inserted, the distal vacuum lead is pinched off and the vacuum then proximately applied until the cement has hardened.

The '030 patent specifically teaches against the use of bone cement under the so-called bone lavage and high pressurizing technique due to the disclosed number of fatalities resulting from such use. The method disclosed in the '030 patent and the devices used are complex. There thus exists a long felt and unresolved need for a bone screw and method of use of the same which overcomes the disadvantages of the prior art.

Moreover, the screw of the '030 patent, in accordance with one of its preferred embodiments, includes a number of radially extending transverse canals denoted by the numeral 4 in the '030 patent. As described in the '030 patent, the bone screw preferably exhibits several transverse canals, preferably 2 to 9 and more preferably 4 to 6 which contact the longitudinal canal. These holes are disclosed as enabling further increase in the effect of the partial vacuum. The use of numerous radially extending apertures, particularly in the fashion shown in the '030 patent, has the potential deleterious effect of reducing the integrity of the screw itself, i.e., weakening the screw.

Various drug delivery devices are also known, for example in the '030 patent, the screws disclosed therein are described as also having drug delivery capabilities. Nevertheless, the drug delivery capabilities are minimized by the potential lack of integrity of the screw itself and such screws do not offer advantages particularly for re-use which may be desirable in numerous cases.

Suffice it to say that numerous disadvantages exist with currently known methods and apparatus for delivery of material to a desired location. There is thus a long felt need to address these disadvantages through use of a device which is relatively easy to make and use.

SUMMARY OF THE INVENTION

The present invention provides a method and apparatus for the effective delivery of material to a desired location. In accordance with a preferred embodiment of the present invention, a device (e.g., a bone screw) is provided which includes a head portion, a shaft portion, and a tip portion. The head portion further includes an injection site wherein an injection device, such as a syringe, or an attachment mechanism can be removably attached.

In accordance with yet other embodiments of the present invention, devices are disclosed which enable the effective and efficient delivery of material in a reliable manner to diseased sites, the devices being provided with enhanced integrity. In accordance with preferred aspects of this embodiment of the present invention, such devices are particularly configured for repeated use.

BRIEF DESCRIPTION OF THE DRAWING

The present invention will hereinafter be described in conjunction with the appended drawing figures wherein like numerals denote like elements.

FIG. 9 is a side view of a device in accordance with one embodiment of the present invention in the form of yet another bone screw;

FIG. 10 is a cross-sectional view showing one application of the device in accordance with the present invention, such as in the form of the bone screw of FIG. 9 in connection with a pedicle attachment to a spinal vertebrae.

FIG. 11 is an exploded perspective view of one of the bone screws shown in conjunction with the application of FIG. 10;

FIG. 15 is an exploded perspective view of a delivery device shown in conjunction with an attachment mechanism of the type shown in FIG. 14 together with a device in the form of a bone screw in accordance with the present invention;

FIG. 15A is a cross-sectional view of the fully assembled delivery mechanism of FIG. 15.

DETAILED DESCRIPTION OF PREFERRED EXEMPLARY EMBODIMENTS OF THE INVENTION

While the way in which the present invention addresses the various disadvantages of prior art devices will be described in greater detail hereinbelow, in general, the present invention provides a method and apparatus for the enhancement of delivery mechanisms useful in connection with fixation devices for bodily use, which enhancement is obtained by modification of the device to improve fixation without deleteriously effecting the performance of the device.

As previously briefly mentioned, in accordance with its various aspects, the devices of the present invention have various applications. It should be appreciated that the illustrations provided herein are for illustrative purposes only and are in no way intended to limit the scope of the invention as set forth in the appended claims. With this in mind, to aid in describing preferred embodiments of the present invention, reference will be made in this description, to devices in the form of a bone screw and devices in the form of delivery devices. In this context, the term "bone screw" is intended to refer to screws of all type which are presently known or hereafter devised by those skilled in the art for use in connection with the internal fixation of fractures of, for example, human or other animal bones. In this regard, cortical screws, cancellous screws, ASIF screws and machine screws are all contemplated as being within the scope of the screws which can be useful in connection with the present invention. It should be appreciated, however, that any type of fixation device such as pins, nails and the like, which are used internally and/or externally are included within the scope of the present invention. Similarly, the term "delivery device" is intended to be broadly construed to refer to any device configured for insertion into a bone for purposes of delivering to a region within, or on the bone, a particular material. As will be described, such materials include, but are not limited to, medicants, bone growth stimulators and the like.

Figure 1:
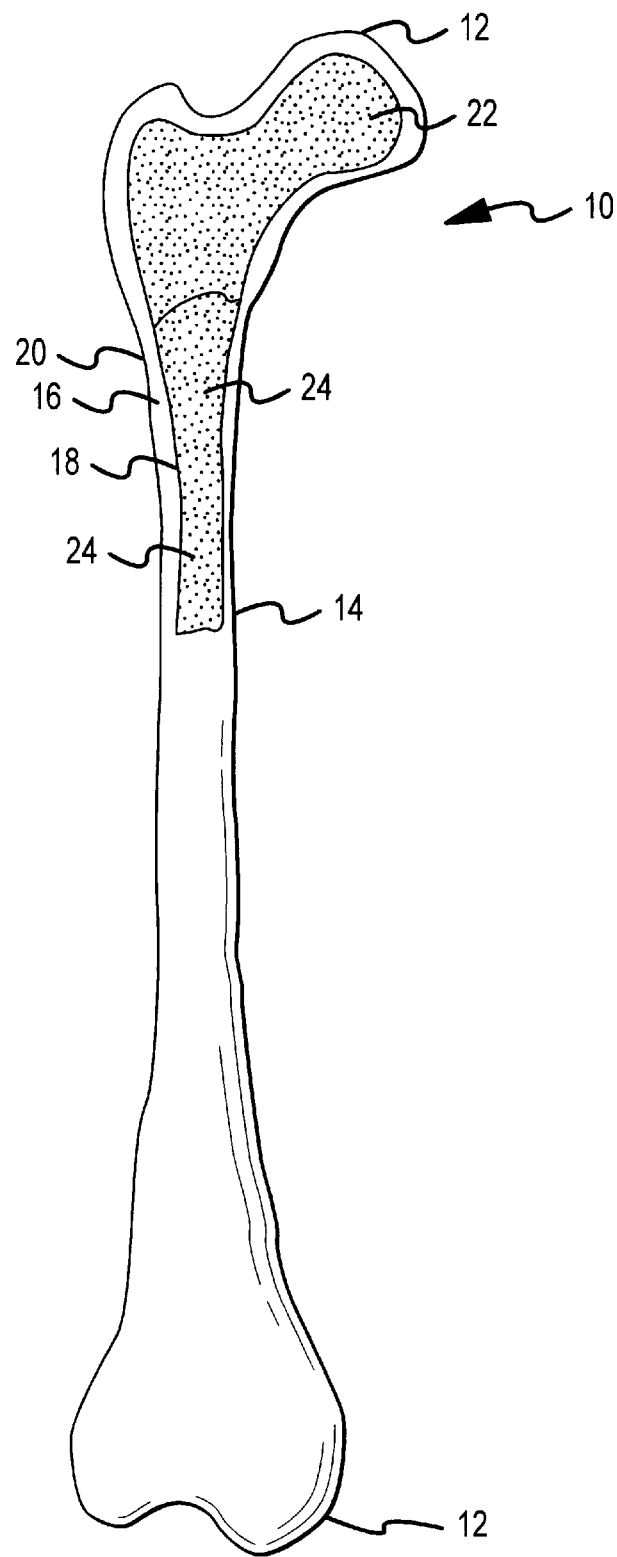
FIG. 1 is a schematic cut-away view of an exemplary long bone.

For purposes of illustration and to provide a point of reference for the following disclosure, referring now to FIG. 1, a typical long bone 10, such as a bone in the arm or leg of a human, suitably includes end portions 12 and a shaft portion 14 spanning therebetween. The cortex 16, as is known, forms the solid and hard outer layer of bone 10. The endosteum 18 and the periosteum 20 portions, respectively, form the inner and outer lining of cortex 16. End portions 12 are suitably filled with cancellous bone 22, and shaft portion 14 is filled with bone marrow 24.

As is known, bones of the type illustrated in FIG. 1 as bone 10 can become weakened due to, for example disease and/or injury. For example, in old age, bones may loose minerals and become porous. Such porous bones tend to be brittle and slower to heal. Various other diseases or conditions of the bone can also result, for example those which tend to result from insufficient supplies of vitamins or minerals or those resulting from stress or overactivity. In general, and as is used herein, a break in a bone is typically referred to as a fracture. With momentary reference to FIG. 2, for example, a fracture 44 may result in bone 10 fracture which may require fixation to enable proper healing. While fracture 44 is shown as being complete, that is extending entirely through the cortex 16 on each side of shaft portion 14 of bone 10, other fractures extending through only a portion of the bone or occurring at any portion or multiple places along the bone such as at the end, are of the type with which the methods and apparatus of the present invention may be used.

As is known, internal fixation of fractures, typically following reduction, can be accomplished through a variety of techniques such as through the use of pins, screws, plates and screws and/or medullary nails. In general, current technologies fail to take into full consideration the condition of the bone which has been fractured. That is, particularly in diseased bone such as osteoporotic bones, the fixation of the bone, such as through the use of screws, is difficult in that the fixation is about a portion which has demonstrated weakness. Thus, fixation, particularly internal fixation of the bone should take into consideration the inherent weakness of the bone which is to be repaired. In this regard, current techniques which involve use of screws to fix the bone, with or without plates, suffer from inherent difficulties in that the fixation is to an inherently weak bone or portion thereof. The present invention addresses this inherent difficulty by providing, as will be described in greater detail hereinbelow, a method and apparatus such that the strength of the fixation to the bone is enhanced through use of the devices and the methods set forth herein.

Figure 2:
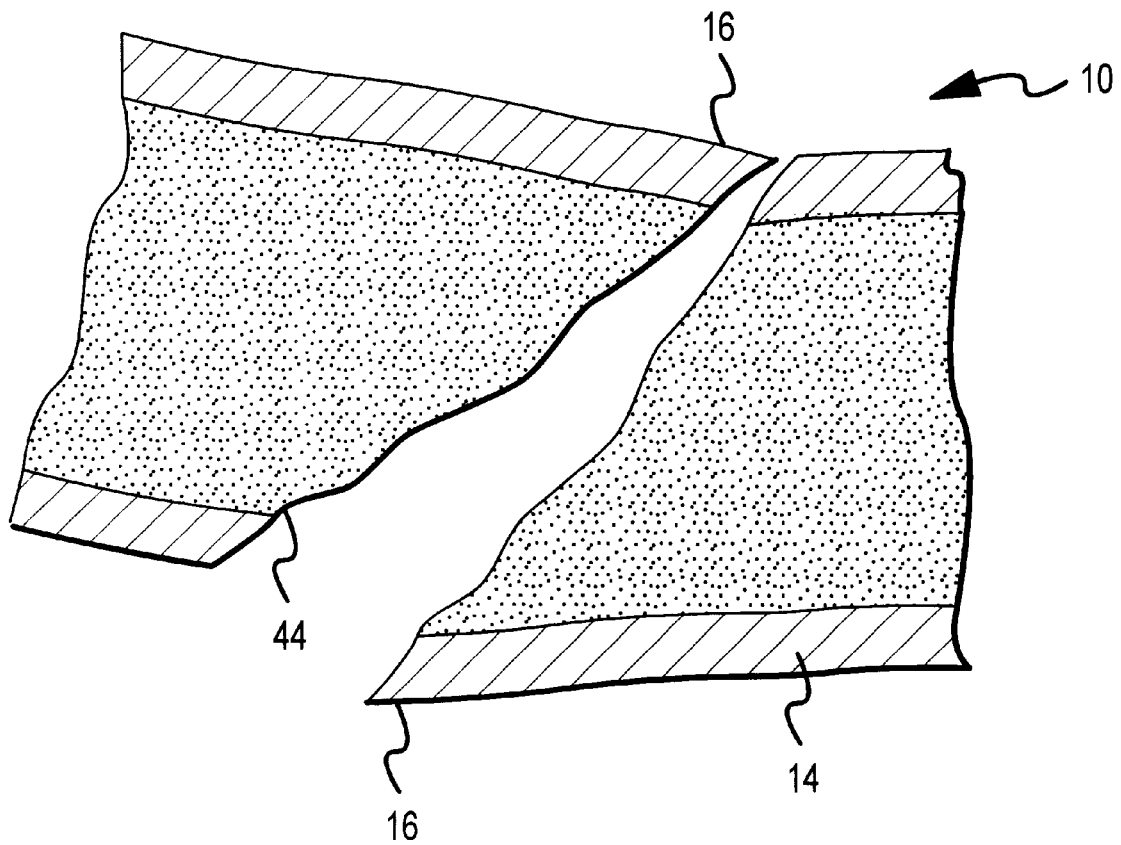
FIG. 2 is a cross-sectional view of a fracture formed in a bone.

As previously noted, although a complete fracture is depicted in FIG. 2, fracture 44 may extend only through a portion of bone 10. Alternatively, bone 10 may be fractured into several pieces. In general, the type and severity of the fracture determines in part the number and type of fixation devices required. For the sake of simplicity, in general, the insertion of a single bone screw 30 will be initially shown and described, such as, for example, in connection with FIGS. 3 and 4. It should be appreciated, however, that screw 30 suitably can be used in conjunction with any number of conventional or hereafter developed fixation devices such as pills, wires, plates, rods and the like to appropriately support and hold bone 10 (none of which are shown in FIGS. 3 and 4).

Figure 3:
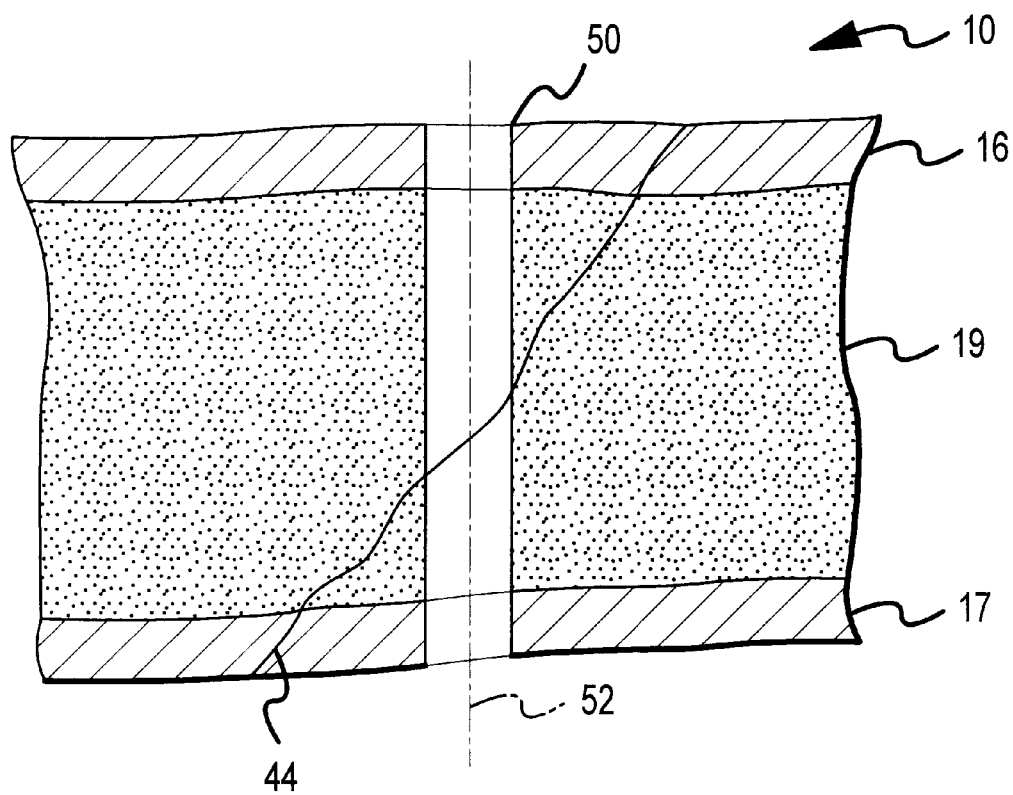
FIG. 3 is a cross-sectional view of an exemplary fracture site in a bone which has been prepared for insertion of a bone screw in accordance with the present invention.

With reference now to FIG. 3, in accordance with one aspect of the present invention, prior to insertion of screw 30, a bore 50 is suitably drilled in bone 10 using methods known in the art. Preferably, bore 50 has an associated bore axis 52 which, although illustrated in FIG. 3 as being substantially orthogonal to the longitudinal axis of the bone, may be disposed at any desired angle with respect to the surface of the bone. For example, in complex fractures where multiple bone screws are used, as is known, it can be desirable to place screw 30 perpendicular to the fracture line rather than the surface of the bone.

Bore 50 suitably extends through cortex 16, matter 19 and opposing cortex 16. Matter 19 is suitably filled with cancellous bone 22 (FIG. 1) in the ends of long bones and filled with bone marrow 24 (FIG. 1) in the shaft of long bones. In certain applications, bore 50 may extend only partly into cortex 17 or not at all. For example, when bone screws are used in conjunction with a fixation plate, the screws used to secure the ends of the plate may be inserted through only one cortex to reduce stress at the ends of the plate.

Figure 4:
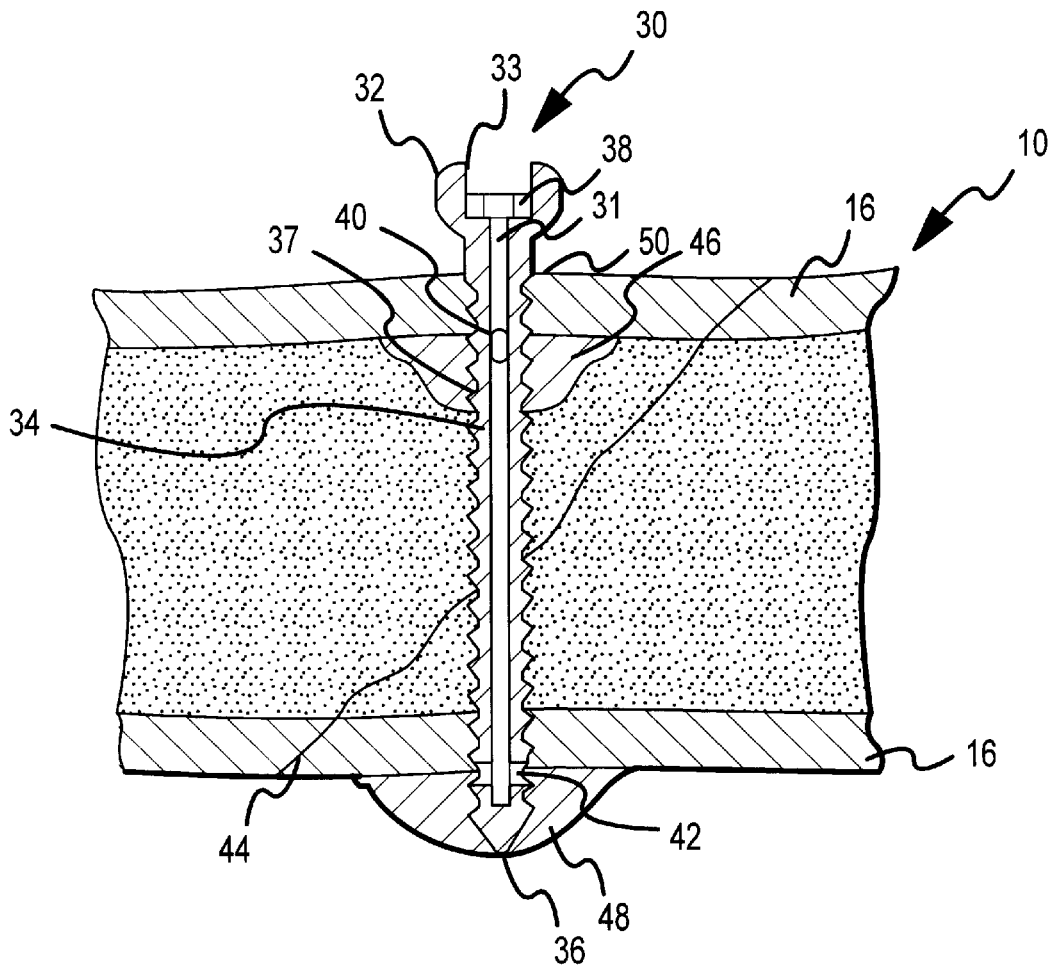
FIG. 4 is a cross-sectional view of a device in accordance with one embodiment of the present invention in the form of a bone screw which is inserted into the fracture site shown in FIG. 3.

With reference now to FIG. 4, bone screw 30 is suitably inserted into bore 50. Although screw 30 may be directly inserted into bone 10, pre-drilling bone 10 with bore 50 preferably reduces the likelihood that bone 10 will splinter as screw 30 is inserted into bone 10. Additionally, bore 50 facilitates more accurate placement of screw 30 in bone 10. Suitable sizing of bore 50 can be determined from known techniques, which for ease of description, will not be herein detailed.

In accordance with one embodiment of the present invention, screw 30 preferably evidences the configuration of a standard cortex screw having a proximal (or top) end 32, a distal (or bottom) end 36 and a shaft 34 spanning therebetween. In accordance with the various exemplary embodiments of the present invention described herein, screw 30 is preferably formed in one piece from any number of strong materials, such as steel, titanium alloys, and the like. Additionally, bone-growth agents can be applied to screw 30 to promote bone growth around screw 30 thereby further securing screw 30 within bone 10.

Shaft 34 preferably evidences threads 37. Threads 37 suitably evidence a major diameter, (i.e., two times the radius measured from the center line of screw 30 to the crest of a particular tooth) and a minor diameter, (i.e., two times the radius measured from the center line to the bottom of a tooth) and a pitch. The major and minor diameters may be selected as appropriate for a particular application, as may be the pitch.

As shown, in this embodiment, screw 30 evidences threads 37 formed substantially along the entire length of shaft 34. It should be appreciated, however, that threads 37 may be formed along only a portion of shaft 34, or intermittently upon various portions of shaft 34, depending upon any particular application.

Distal end 36 suitably forms a tip which is preferably cone-shaped. In accordance with the illustrated embodiments, tip 36 evidences a closed end. It should be appreciated, however, as will be described in greater detail in connection with various other embodiments of the present invention, that tip 36, in certain applications, may be open. Although not shown, tip 36 may be provided with cutting flutes or otherwise be configured in a self-tapping manner.

As shown best in FIG. 4, screw 30 preferably evidences an axial bore 31 which spans from head 32 in proximity to tip 36. Bore 31 may be formed in any suitable fashion. For example, in accordance with various aspects of this embodiment of the present invention, bore 31 may be formed in the configuration of a cannulated bone screw, and as previously briefly noted, extend through the entire length of screw 30, or as shown, include a closed distal or bottom end.

In accordance with a preferred aspect of the present invention, top head 32 is suitably configured to exhibit an appropriate external profile and an appropriate internal profile. In this regard, in general, the external profile of head 32 is suitably configured for receipt of any suitable driving device. In the context of bone screw 30 illustrated in FIGS. 3 and 4, head 32 suitably exhibits a geometric configuration suitable for receipt of a handle or other suitable driving device useful for turning screw 30 into bore 50.

The internal profile of head 32 preferably includes a recess 38. Preferably, recess 38 is suitably configured to either aid in insertion of screw 30 into bore 50, enable receipt of a fluid delivery device, or both. As illustrated in FIG. 4, in accordance with one aspect of this embodiment of the present embodiment, recess 38 evidences a tapped top which communicates with bore 31 as will be described hereinbelow. Such a tapped top is suitable for receipt of a syringe or other fluid delivery device. Head 32 may be suitably configured for any particular application. For example, as shown in the illustrated embodiment of FIG. 4, head 32 can be provided with a beveled or curved lower surface in proximity between head portion and shaft portion 34 of bone screw 30. In this manner, stress and strain which can tend to concentrate at the interface between head portion 32 and shaft portion 34 can be minimized.

It should be appreciated that the external and internal profiles of head 32 may be adapted for any particular application. As will be described in greater detail hereinbelow, in accordance with various aspects of the present invention, the internal profile of head 32 is suitably configured to aid in the attachment of a fluid delivery device. In accordance with other aspects of the present invention, however, the internal profile of head 32 may be configured in any form which is suitable for receipt of such a fluid delivery device. Similarly, the external profile of head 32 may be configured in any fashion suitable to enable insertion of screw 32 into, for example, bore 50.

In accordance with a preferred aspect of this embodiment of the present invention, screw 30 is suitably provided with one or more radially extending slots, for example, the respective illustrated slots 40 and 42. As will be described in greater detail hereinbelow, the number, location and configuration of slots 40, 42 may be varied for any particular application. In accordance with the illustrated embodiment, slot 40 is suitably located in proximity to the proximal portion of screw 30, and slot 42 is suitably located in proximity to the distal portion of screw 30. Slots 40, 42 preferably extend radially outwardly from bore 31, and as will be described hereinbelow, aid in the delivery of an injectable material into a desired region of interest during use of screw 30. As shown in FIG. 4, in accordance with this embodiment, slot 40 is suitably positioned along the length of screw 30 such that when it is placed within bone 10, slot 40 is oriented with respect to the endosteum 18 of cortex 16. Further, in accordance with this embodiment of the present invention, slot 42, when screw 30 is positioned within bone 10, is suitably positioned in proximity to the periosteum 20 of the lower most portion of cortex 16, as such is shown best in FIG. 4.

In accordance with various aspects of the present invention, slots 40, 42 are suitably positioned along shaft 34 of bone screw 30 so as to provide a suitable exit for material injected into bore 31 but in a manner which is calculated to minimize the effect of inclusion of slots 40, 42 on the structural integrity of screw 30. While any number and orientation of slots 40, 42 may be appropriate in a particular application, preferably, and in accordance with preferred aspects of the present invention, slots 40, 42 are placed in proximity to threads 37 so as to not impede the performance of threads 37. Stated another way, preferably slots 40 and 42 are placed above the grooves forming threads 37 so as to not impede or otherwise interfere substantially with the performance of the adjacent thread. For example, slots may be placed such that they fit within the pitch of the thread in an appropriate and suitable fashion. The present inventors have found that locating the slots in such fashion tends to minimize the effects of inclusion of slots 40, 42 on the integrity of screw 30. It should be appreciated, however, that in some applications the precise location of a particular configuration slot to be provided in the context of any screw 30, particularly where more than one slot is provided in any particular screw, the precise location may be such as to fall outside of the pitch of any particular thread. For example, slots may be provided along the shaft or non-threaded portion of screw 30.

Slots 40, 42 may also be aligned in any suitable fashion. In accordance with a preferred aspect of the present invention and as shown in the illustrated embodiment of FIG. 4, slots 40 and 42 may be orthogonally aligned. For example, as shown in FIG. 4, the central axis of slot 40 is orthogonal to the central axis of slot 42. It should be appreciated, however, that other alignments may be used. For example, slots 40 and 42 may be similarly aligned and extend radially outwardly from bore 50 in a substantially identical fashion. Alternatively, three slots (not shown) may be positioned to radially extend outward from the central bore at equidistant locations (i.e., 120 degrees). Further, slots 40, 42 may be aligned in an angular orientation which is greater than or less than 90 degrees. That is, the slots may be angled upwardly or downwardly and offset from a typical radial orientation. In general, any number and orientation of slots as may be desirable for a particular application can be used in accordance with the present invention. Nevertheless, in accordance with a preferred embodiment, orthogonal orientation of the slots tends to enhance rigidity and strength of screw 30.

As used herein, the term "slot" refers to any radially extending aperture which extends from the outer most portion of screw 30 into and in communication with bore 31. Injectable material injected into bore (cannula) 31, is suitably delivered to desirable delivery sites by slots 40, 42, which preferably extend radially outward from cannula 38. In this manner, bone cement delivered through slots 40 and 42 harden to form respective cement masses 46 and 48 near cortex 16 to secure screw 30 to bone 10.

Slots 40 may suitably exhibit any geometric configuration for example, round or circular, star-shaped or other geometric configurations as may be appropriately used. In accordance with a preferred aspect of the present invention, and as shown in the illustrated embodiment of FIG. 4, slots 40 and 42 exhibit a generally oblong or oval geometric configuration.

The transverse configuration of slots 40 and 42 may also be suitably selected for any particular application. In accordance with a preferred aspect of this embodiment of the present invention, slots 40, 42 exhibit a generally uniform cross-sectional configuration about their length, i.e., the portion extending from bore 31 to the outer most portion of screw 30. It should be appreciated, however, that varying cross-sectional areas may, in appropriate cases, be utilized. Furthermore, the radial orientation of slots 40 and 42 may be selected as may be appropriate for a particular application. In accordance with a preferred aspect of this embodiment of the present invention and as shown in the illustrated embodiment of FIG. 4, slots 40 and 42 extend laterally in a substantially uniform fashion from bore 31 to the outermost portion of screw 30. It should be appreciated, however, that various angular orientations of the radially extending slots may be utilized. For example, slot 40 may suitably be configured to exhibit an angular orientation in a downward fashion or upward fashion. Slot 42 may also be suitably configured.

In accordance with various aspects of the present invention, the cross-sectional areas of slots 40 and 42 are preferably larger than that of cannula 31, thereby facilitating pressure control when material is injected through cannula 31. For example, in accordance with one exemplary embodiment of screw 30, the long diameters of slots 40 and 42 may be on the order of about 2.0 mm, and short diameters on the order of about 1.2 mm for a bone screw 30 wherein the diameter of cannula 31 is on the order of 1.3 mm.

In accordance with a preferred aspect of the present invention, screw 30 is suitably inserted into bore 50 of bone 10 in an appropriate manner, such as by attachment of any suitable insertion device (not shown) attached to head 32. Once screw 30 is thus suitably inserted into bone 10 in proximity to fracture 44, a suitable delivery device (not shown in FIG. 4) is attached to head 32, such as in proximity thereto, and preferably in a substantially sealed manner to recess 38 to provide an inlet for an injectable fluid (e.g., bone cement) which is useful in enhancing the fixation of screw 30 to bone 10. In this manner, and in accordance with one aspect of the present invention, a syringe, cement gun or the like may be suitably attached to head 32, the lower most portion of the syringe communicating with recess 38. The delivery device (not shown) can suitably be filled with an appropriate cement. Any cement useful in connection with conventional fixation devices may be used. Preferably, low viscosity cements are used such as conventional polymethacrylate cements. However, other acrylic cements, resorbable materials and the like may be used as appropriate to aid in fixation of screw 30 to bone 10.

In accordance with one aspect of the present invention, a syringe filled with a suitable cement, is attached to screw 30 such that the cement can be injected into bore 31 of screw 32. As injected, an appreciable amount of cement will be caused to pass through bore 31 and through respective slots 40 and 42 thereby enabling formation of respective cement regions 46, 48 in proximity to slots 40 and 42. As shown in the illustrated embodiment of FIG. 4, regions 46 and 48 serve to enhance fixation of screw 30 to bone 10 by providing support of screw 30 in proximity to the outer most portions, e.g., cortex portions of bone 10.

As will be described herein, various modifications can be made in the orientation of the slots to provide enhanced and/or alternative cement regions which aid in fixation of the devices of the present invention to the bone in regions of interest. In addition, in accordance with various alternative embodiments of the present invention, materials other than acrylic resins, (e.g., bone cements) may be used and delivered to regions of interest.

It should be appreciated, particularly in the context of the embodiment of the present invention illustrated in FIG. 4, that utilization of the device and methods of the present invention enable significant advantages over prior art systems. Particularly, in the case of osteoporotic bones, the provision of cement in proximity to fracture 44 tends to strengthen the fixation of screw 30 about a region of bone 10 which has in such cases demonstrated an inherent weakness. Stated another way, the provision of cement in proximity to both the inner and outer portions of bone 10 serve to fix screw 30 in a manner which has heretofore been unavailable through prior art devices and techniques.

Having now described the foregoing exemplary embodiment of the present invention, illustrated in FIG. 4, various modifications in the design and arrangement can be made and are contemplated in connection with the present invention. As such, modifications as will be contemplated in light of the foregoing disclosure may be numerous, this application serves only to illustrate various applications and modifications. These modifications are provided for illustrative purposes only and are not intended in any way to limit the scope of the subject invention.

Figure 5B:
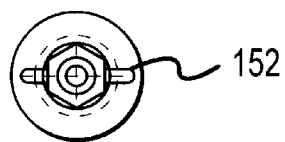
FIG. 5B is a top view of a device in accordance with one embodiment of the present invention, such as the top view of the bone screw of FIG. 5.
Figure 5:
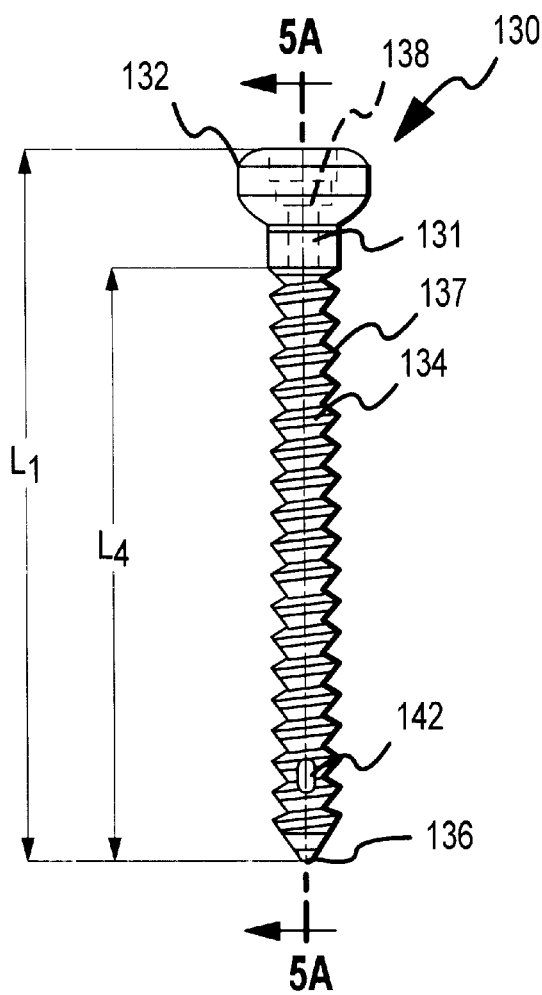
FIG. 5 is a side view of a device in accordance with one embodiment of the present invention in the form of a bone screw.
Figure 5A:
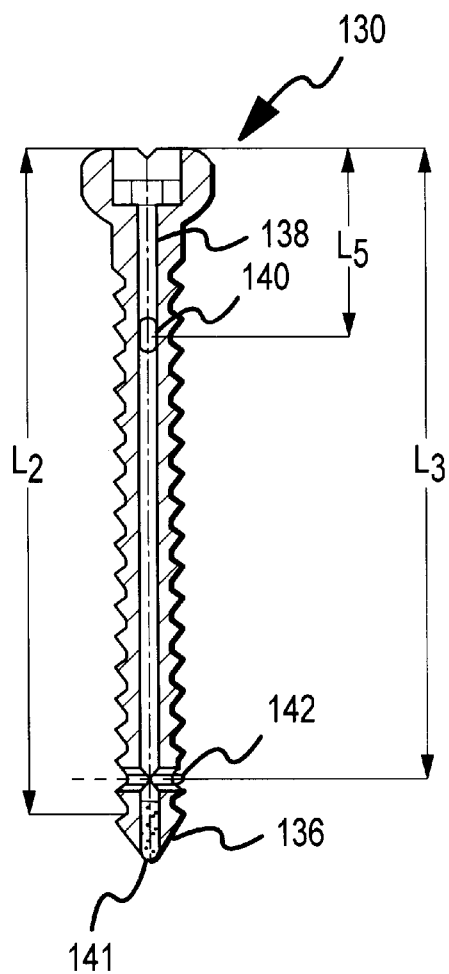
FIG. 5A is a cross-sectional view of the bone screw shown in FIG. 5 taken through line 5—5.

In this regard, and with reference now to FIGS. 5 and 5A, a further embodiment of a device in accordance with the present invention is shown. Specifically, a device in the form of a bone screw 130 is shown as evidencing a length $L_1$. Length $L_1$ may be any appropriate dimension depending on the particular application for which bone screw 130 is desired. Screw 130, like screw 30 of FIGS. 3 and 4, suitably includes a head portion 132, a tip portion 136 and a shaft 134 spanning therebetween. Shaft 134 suitably includes a plurality of threads 137 spanning a length $L_4$. As previously briefly noted, length $L_4$ may be equal to or less than length $L_1$. Head 132 is suitably provided with a fluid receiving region 138 internally thereof. Head 32 suitably exhibits an internal or external profile appropriate for receipt of a conventional driving tool. An internal bore or cannula 131 extends about the length $L_1$ of screw 130. In contrast to screw 30, cannula 131 extends about the entire length of screw 130. In certain applications, to control the flow of the injectable material, a plug 141 may be inserted into the distal end of tip 136. Respective radially extending slots 140 and 142 are suitably provided at discrete points about shaft 134. Preferably, bore 140 is located at a distance of $L_5$ from top or head 132 of screw 130. Length $L_5$ may be suitably selected for appropriate positioning of bore 40 for any particular application. Similarly, bore 142 is suitably provided at a distance $L_3$ from head 132; again, the length of $L_3$ may be suitably selected for any particular application. In accordance with a preferred aspect of the present invention, the sum of lengths $L_3$ and $L_5$ exceeds the length $L_1$ of screw 131. However, in appropriate circumstances, the sum of lengths $L_3$ and $L_5$ may be equal to or less than the length $L_1$ of screw 131.

With reference now to FIG. 5B, screw 132 may be suitably provided with appropriate markings 152 proximate head 132. With momentary reference to FIG. 5B, the top of head portion 132 of screw 130 in accordance with one embodiment of the present invention may be provided with appropriate markings 152. Markings 152 advantageously are oriented such as to position screw 130 and to indicate alignment of one of the plurality of slots, most preferably the alignment of slot 140. Such alignment may be made at the time of insertion or thereafter; for example, screw 130 can be aligned even after insertion into bone 10 to aid in delivery of injectable material to a specific location within bone 10. Although not acceptable in some cases, alignment may also be effected even after injection of the cement, but preferably prior to curing.

Various other modifications may be made in the devices in accordance with the present invention. For example, with reference now to FIG. 6, a bone screw 230 may be suitably provided. Screw 230 preferably comprises a top 232, a distal end 236 and a shaft 234 extending therebetween. Shaft 234 suitably exhibits a plurality of threads 237. At least one, and preferably a plurality of slots 240, 242 are suitably provided in screw 234, which slots suitably extend radially outwardly from a central cannula 231 to the outer most portion of screw 230. Screw 230 is thus similar to screws 30 and 130, however, in the context of the illustrated embodiment of FIG. 6, slots 240 and 242 are axially aligned. Stated another way, and as is shown, slots 240 and 242 radially extend about a substantially aligned plane co-extensive with the axis of cannula 231.

Figure 6:
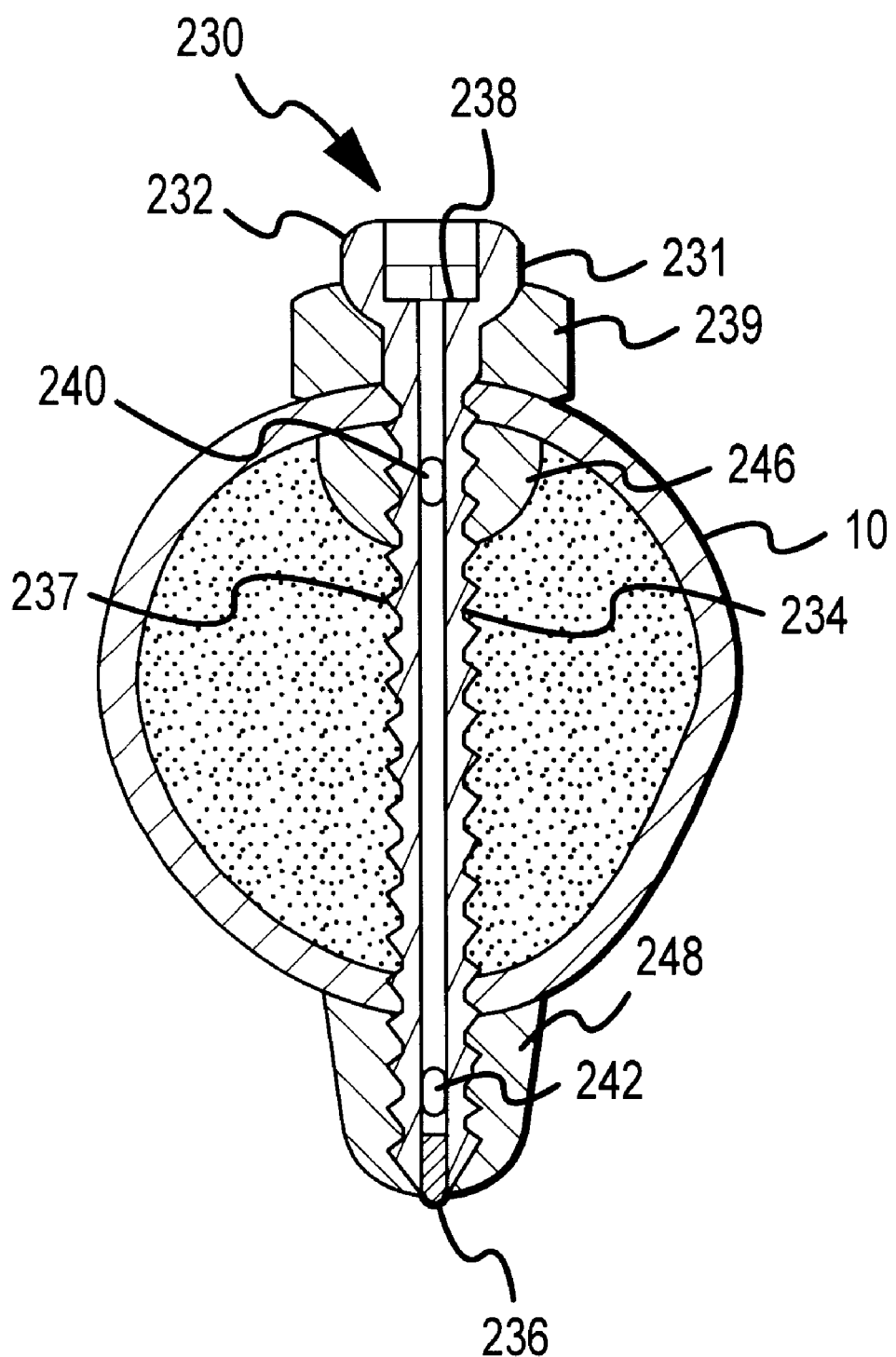
FIG. 6 is a cross-sectional view of a device in accordance with one embodiment of the present invention in the form of a bone screw useful in mending a fracture of an osteoporotic bone.

As shown in FIG. 6, screw 230 may be suitably configured for use in connection with a bone plate 239, preferably of conventional configuration. As is known, in connection with serious fractures it may be appropriate to internally fix bone 10 through use of plate 239 into which a plurality of screws (e.g., screws 230) are received. In a fashion similar to use of screw 30, screw 230 may be suitably inserted into bone 10; however, in the case of this embodiment with use of plate 239, screw 230 is initially inserted through plate 239 as it is introduced, it passes through the plate and also into the upper most portion of bone 10. Once so inserted, injectable material may be inserted by communication of a delivery device (not shown in FIG. 6) with receiving region 238 of top 232. As will be described in greater detail hereinbelow in connection with further exemplary embodiments of the present invention, cement may be first injected in proximity to bore 242, such as, for example, through use of an extending distribution device attached to the delivery device (both not shown). In this manner, cement may be initially delivered in proximity to bore 242; once so delivered, extension device may be removed, delivery device re-attached to screw 230 and cement delivered in proximity to top 232. In certain applications, multi-step cement introduction may be appropriate.

Figure 7:
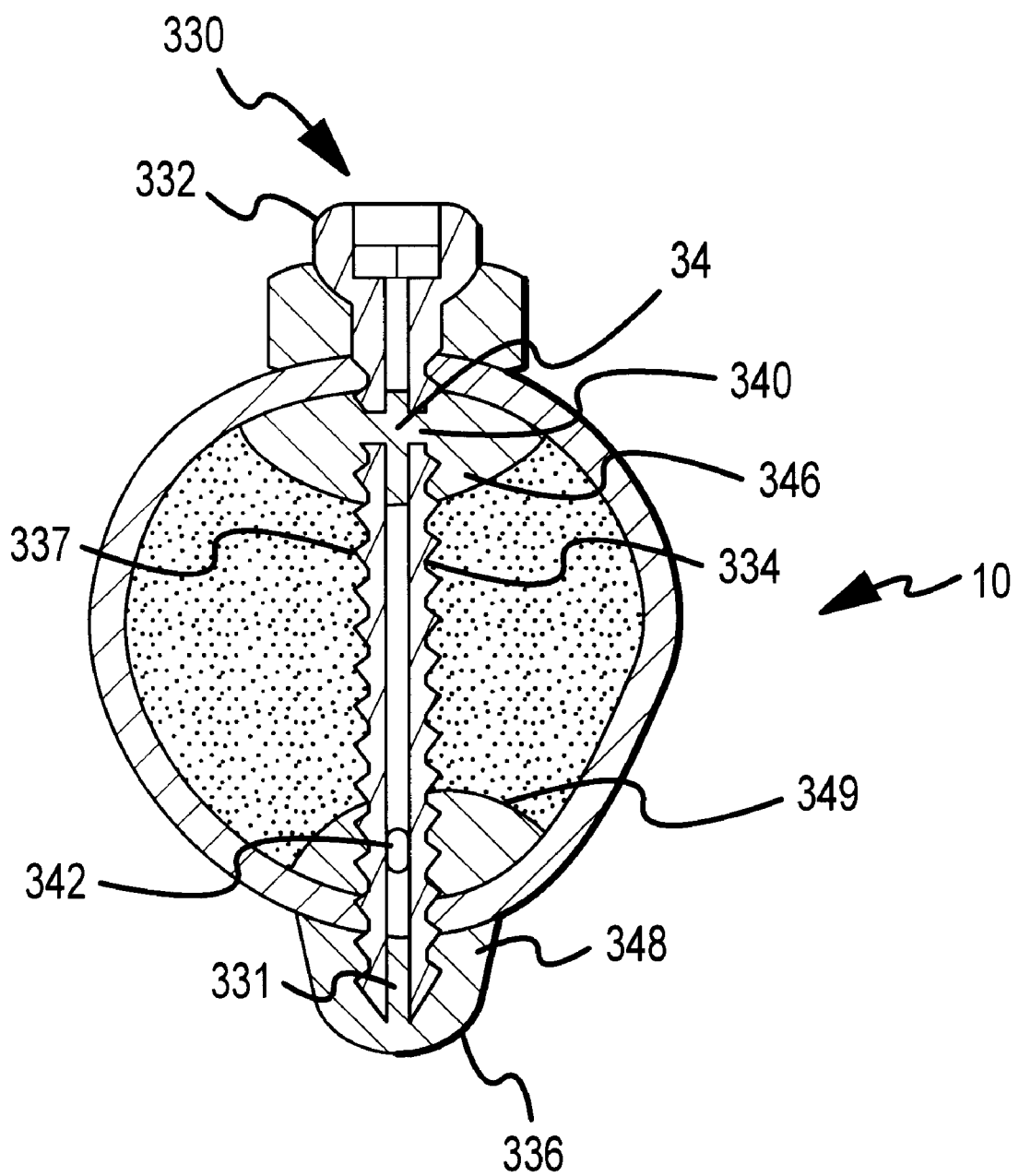
FIG. 7 is a cross-sectional view of a device in accordance with one embodiment of the invention in the form of another bone screw provided with a plurality of delivery apertures.

With reference now to FIG. 7, multiple delivery sites may be provided in any particular device (e.g., bone screw) useful in the context of the present invention. In accordance with this exemplary embodiment of the present invention, a bone screw 330 is provided which includes a top 332, a distal end 336 and a shaft 334 extending therebetween. Shaft 334 suitably exhibits threads 334 carried on the outermost portion thereof. A cannula 331 extending from top 332 about the entire length of screw 330, that is entirely to and through distal end 336 may be suitably provided. Screw 330 suitably also includes respective radially extending ports 340 and 342, which, as shown, are preferably orthogonally aligned relative to the axis of screw 330.

In use screw 330 enables for the formation of respective cement regions 346, 348 and 349. Specifically, in the context of use of screw 330 cement is injected, as described hereinabove, into cannula 331 and cement is forced out of screw 330. Cement is injected into screw 330 via cannula 331 and caused to exit cannula 331 in proximity of tip 336 to form cement region 348. Similarly, cement is caused to exit in proximity to slot 342 to form cement region 349 and in proximity to slot 340 to form cement region 346. In this manner, as is shown, significant support is engendered about screw 330 in proximity to distal end 336 on both the inner and outer sides of bone 10.

Figure 8B:
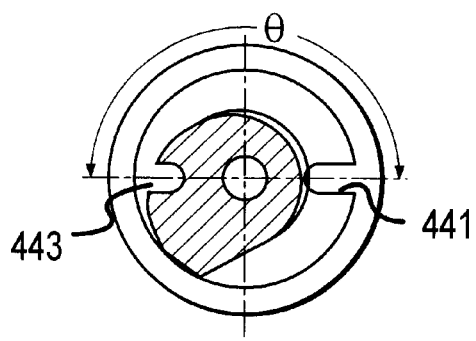
FIG. 8B is a top view of one embodiment of the bone screw of FIG. 8 showing the incorporation of a channel groove vent.
Figure 8:
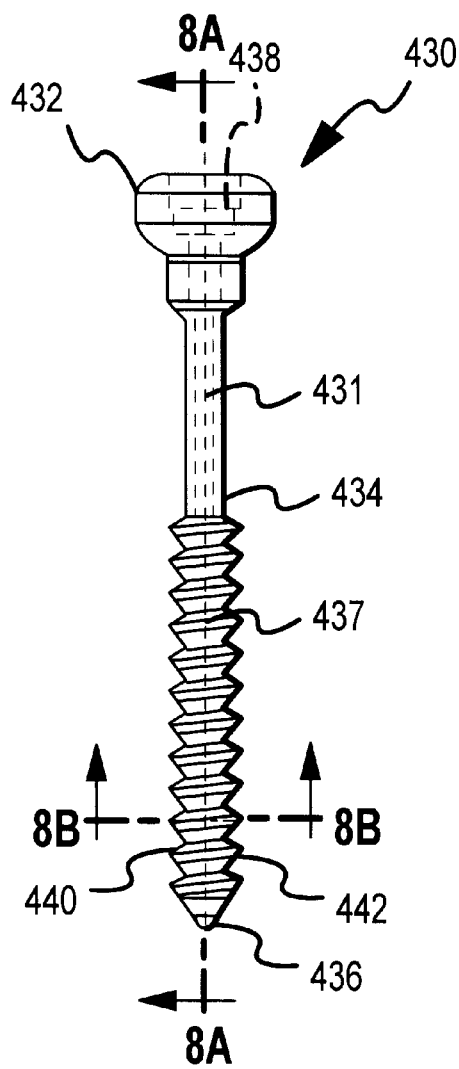
FIG. 8 is a side view of a device in accordance with one embodiment of the present invention in the form of yet another bone screw.
Figure 8A:
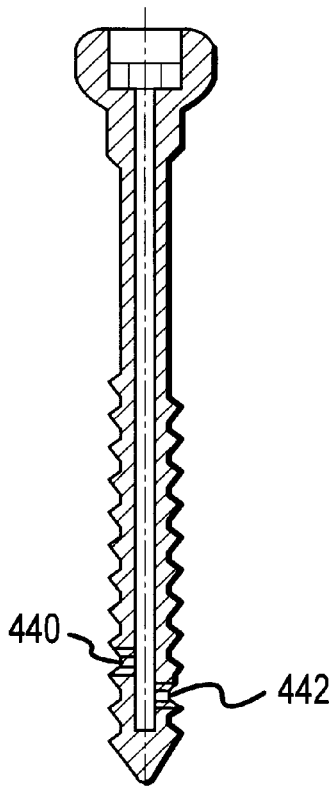
FIG. 8A is a cross-sectional view of the bone screw of FIG. 8.

With reference now to FIG. 8, a further embodiment of the present invention will now be described. In accordance with a preferred aspect of this embodiment of the present invention, a screw 430 is provided which is of the general configuration of a cancellous screw. As is known, cancellous screws tend to have larger threads and are frequently used in metaphyseal areas. In general, they are threaded, as is shown, only about a portion of the length thereof. Specifically, and in accordance with preferred aspects of this embodiment of the present invention, screw 430 evidences a head 432, a tip 436 and a shaft 434 extending therebetween. As shown, shaft 434 is provided with a plurality of threads 437; however, threads 437 extend only about the bottom portion thereof thereby leaving a smooth shaft portion in the proximal portion of shaft 434. Preferably, as shown in FIG. 8A, the threaded section of shaft 434 preferably evidences a larger thread than, for example, the threads of screws 330, 230, 130 and 30. In this fashion, screws 430 are suitable for use in soft cancellous bones in that the threads provide more purchase therein.

Screw 430 is provided with a central cannula 431 which extends from top 432 through the length of screw 430, but which cannula 431 does not extend through the entirety of screw 430. That is, tip 436 evidences a closed configuration. Respective slots 440 and 442 are provided in proximity to distal end 436. Head 432 is suitably configured to exhibit an external profile capable of adapting to an appropriate driving tool. Head 432 is further suitably configured to exhibit an internal recess 438 for receipt of an appropriate fluid containing device.

Preferably, as shown best in FIG. 8A, respective slots 440 and 442 are closely positioned relative to one another. Preferably, as previously noted, slots 440 and 442 are suitably provided in a manner which is calculated not to significantly impede the strength or performance of screw 430. Slots 440 and 442 of screw 430 are suitably arranged in any convenient fashion in proximity to distal end 436. Preferably, and in accordance with a preferred aspect of this embodiment of the present invention, slots 440 and 442 are suitably provided as radially extending transverse paths from slot 431 to the outermost portion of screw 430. Preferably, as shown best in FIG. 8A, slots 440 and 442 are oriented within the pitch of the thread.

In accordance with a preferred aspect of this embodiment of the present invention, screw 430 is provided with respective channel groove vents 441 and 443 which preferably extend about the length, or a portion thereof, of shaft 434. In accordance with a preferred aspect of this embodiment of the present invention, and with continued reference to FIGS. 8 and 8B, channel groove vents 441, 443 are suitably provided about a portion of screw 430 which extends upwardly (e.g., proximately) of slots 440 and 442. However, in accordance with various alternatives of this embodiment of the present invention, vent grooves 441 and 443 may be provided about the entire length thereof.

As will be appreciated by those skilled in the art, in certain applications it is desirous to provide a channel for evacuation of material which is displaced by introduction of cement into the bone. In accordance with conventional practices, which in various applications may be utilized in connection with the screws disclosed herein, venting is obtained by drilling a vent hole adjacent the bore (for example bore 50) which bore (i.e., vent) provides a channel for exiting of materials which are displaced when cement is inserted into the bore, such as via bone screw 430. In general, as shown best in FIG. 8B, vent grooves 441 and 443 are suitably provided by cutting from the major to minor groove of the thread pattern 437 of shaft 434. Provision of vent grooves 441 and 443, in the context of the present invention, enables material to be displaced in proximity to screw 430 and avoids the necessity of further drilling for vent purposes in proximity to the entry point of screw 430.

Although vent grooves 441 and 443 are shown as being generally in line with slots 440 and 442, alternative configurations may be utilized. For example, vents 441, 443 may be skewed relative to the angular orientation of slots 440 and 442, or such may be provided in various angular orientations relative to the other. For example, although as shown in FIG. 8B the angle theta which separates the center most portion of groove 441 and groove 443 is on the order of 183 degrees. Angles theta of less than 180 degrees may be acceptable in appropriate applications.

With reference now to FIG. 9, the heads of the various screws and other devices disclosed herein may be modified for appropriate applications. For example, in the context of spinal attachment devices, the heads of the screws useful in the context of the present invention may be modified for receipt of external or internal (but external to the bone) support structures. With continued reference to FIG. 9, a screw 530 in accordance with this embodiment of the present invention preferably comprises a head 532, a tip 536 and a body 534 extending therebetween. Head 532 is preferably provided with an articulating top 533 which is suitably configured in the form of a ball. As will be described in connection with FIGS. 10, 11 and 12, articulating top 533 easily enables positioning of screw 530 in a vertebra and attachment to screw 530 of the various support mechanisms and devices which are used in spinal fixation structures.

Preferably, and as shown, screw 530 evidences a central bore 531 which extends only about a portion of screw 530. Respective slots 540 and 542 are suitably provided in proximity to tip 536, slots 540 and 542 extend radially from cannula 531 outwardly to the outermost portion of screw 530.

As is shown best in FIG. 10, screws of the type shown in FIG. 9, namely screws 530A and 530B are suitably configured for pedicle insertion to enable the formation of a support structure, in a conventional fashion, parallel to the spinal column. In this fashion, distal ends 536A, 536B of screws 530A and 530B are inserted into the respective centra of the vertebrae in a fashion similar to the insertion techniques described hereinabove. Other spinal applications, of course, may also be accomplished through use of the methods and apparatus disclosed herein.

Figure 12:
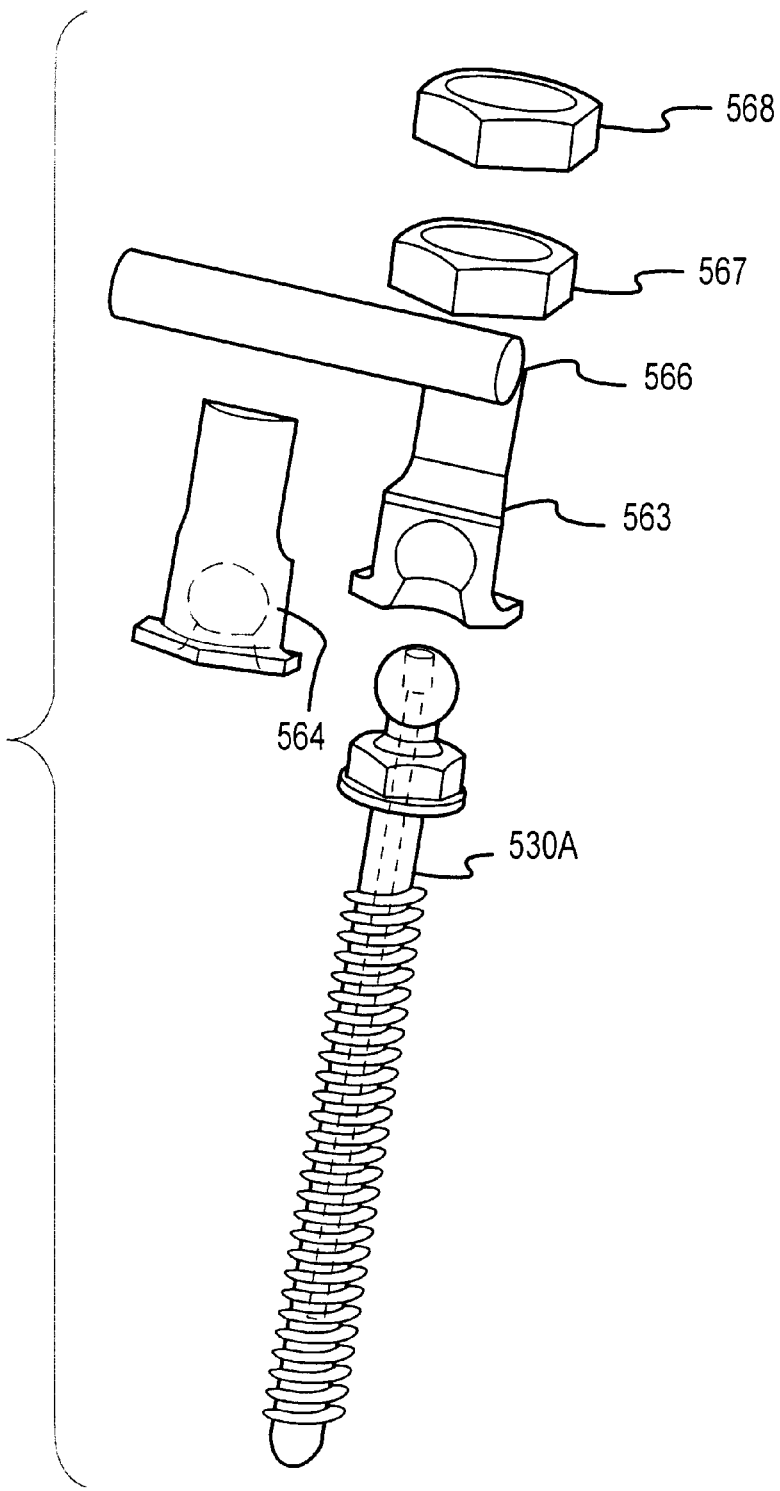
FIG. 12 is an exploded perspective view of another of the bone screws shown in the application of FIG. 10.

As shown in FIGS. 10–12, in accordance with this aspect of the present invention, screws 530A and 530B may be used as anchors for internal fixation devices. In contrast to external fixation devices, internal fixation devices are installed without extending through the skin of the patient, and thus, typically require low profile attachment to bone.

After screws 530A and 530B are suitably seated within a bone mass, a syringe or other suitable injection device is attached to respective recesses 538A, 538B in respective heads 533A and 533B. In a manner as previously described herein, bone cement is suitably delivered through respective cannulas 531A and 531B to secure screws 530A and 530B within the bone mass and create, for example, respective cement masses 560 and 562.

After the screws have been secured, appropriate fixation components may be attached to articulating heads 533A and 533B. For example, and with specific reference now to FIG. 11, sleeves 563 and 564 may suitably couple a fixator rod 566 to screw 530A. A bottom nut 567 is suitably tightened about sleeves 563, 564. Sleeves 562, 564 are caused to tighten over head portion 533A and fixator rod 566 is suitably disposed between sleeves 563, 564 and is secured by a top nut 568.

In a similar fashion, and with reference now to FIG. 12, a fixator rod 570 may be suitably coupled to screw 530B using collar arrangement suitably comprising respective sleeves 574 and 576. Respective sockets formed in sleeves 574 and 576 suitably tighten over articulating head 533B and rod 570 is received in a receiving portion 577 of sleeve 574. Preferably, a retaining nut 575 is suitably adhered to the uppermost portions of sleeves 574 and 576, such as is shown in FIG. 10, thereby enabling assembly of the fixation device to articulating head 533B of screw 530B. As shown in FIGS. 10 and 11, preferably, screw 530B is configured to provide for a second delivery port 577, which port can be used to facilitate the delivery of a material (e.g., adhesives) through screw 530B. One of the advantages which can be obtained through use of fixation devices of the type described herein is in alignment of the particular fixation components. That is, given an articulating head, i.e., alignment can be obtained after insertion of screws 530A and 530B.

In certain applications it may be desirable to prefill the devices, e.g., screws disclosed herein. For example, the screw, such as screw 530B may be filled with an injectable material, e.g., adhesive, medicant or otherwise, prior to insertion into the bone.

As described briefly hereinabove, preferably the devices in accordance with various aspects of the present invention are used in conjunction with delivery devices to facilitate the delivery of injectable materials (e.g., fluids) into a region of a bone. In this regard, the present inventors have found that in various applications it may be desirable to utilize an adaptor to facilitate the substantially fluid tight delivery of the injectable material into the various bone screws disclosed herein.

Figure 13:
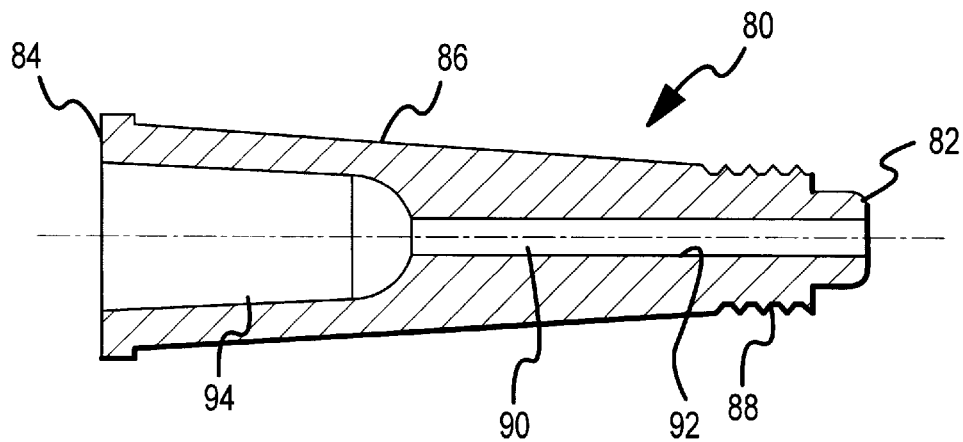
FIG. 13 is a cross-sectional view of an attachment mechanism useful in conjunction with the devices in accordance with the present invention.

With reference now to FIG. 13, in accordance with one embodiment of this aspect of the present invention, an adaptor 80 is provided which includes a first end 82, a second end 84 and a body 86 spanning therebetween. Preferably, in proximity to end 82, body 86 exhibits a threaded region 88. An internal bore 90 is suitably provided about the axis of adapter 80 and includes a first end 92 and a second end 94. Preferably, first end 92 includes a central cannula and second end 94 includes an enlarged recessed region suitable for receipt of a syringe tip. Adapter 80 may be utilized in conjunction with any of the screws or other devices disclosed herein. For example, adaptor 80 may be configured for use in connection with bone screw 30. In such case, recess 38 of head 32 will be suitably configured to receive threaded region 88. Adapter 80 may be utilized in conjunction with bone screw 30 either before and/or after insertion into bone 10. For example, in the event adapter 80 is affixed to screw 30 prior to insertion of screw 30 into bone 10, end 84 is suitably configured for receipt of an appropriate driving mechanism (e.g., screwdriver, wrench or the like). Alternatively, once screw 30 is inserted into a bone region, adapter 80 may be applied to facilitate the substantially fluid tight delivery of cement or other fluids into the bone 10.

In lieu of utilizing adapter 80, in accordance with various aspects of the present invention, in order to provide a fluid tight seal, the syringe or other fluid delivery device used for delivery of the injectable fluid may be suitably provided with threads, such as in the form of threads 88, which threads can be used to engage corresponding threads contained in the top portion, for example top portion 32, of screw 30.

Figure 14:
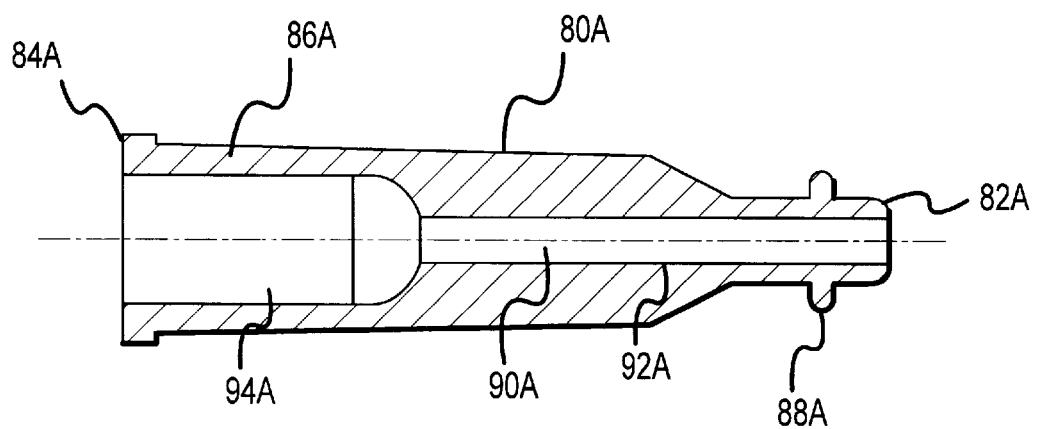
FIG. 14 is a cross-sectional view of a further embodiment of an attachment mechanism useful in conjunction with the devices in accordance with the present invention.

With reference now to FIG. 14, adapter 80 may be suitably configured to exhibit a quick connect-disconnect portion in lieu of threads 88. In this regard, adapter 80A suitably includes a first end 82A, a second end 84A and a body 86A substantially spanning therebetween. Screw 80A suitably includes an internal bore 90A spanning the length thereof including a first portion 92A and a second portion 94A. In the context of this particular aspect of this embodiment of the present invention, end 82A is suitably provided with a key-like quick connect-disconnect protrusion 88A, which protrusion suitably corresponds with corresponding receiving portion located in the top, for example top 32, of the bone screws disclosed herein.

In this regard, and in connection with the exploded depiction shown in FIG. 15, quick connect-disconnect end 88A of adapter 80A may be suitably configured for attachment to screw 30 such as in proximity top portion 32 thereof. A fluid delivery mechanism 95 suitably including an injectable fluid 96 for delivery into a bony region is provided for communication with adapter 80A in proximity to end 84A. Fluid delivery mechanism 95, for example in the form of a syringe, may be of any conventional type, such as conventional slip-tip syringes, large catheter tip syringes and/or tapered or sleeve syringes. Other delivery devices as are now known or hereafter devised by those skilled in the art may also be utilized. In the context of this embodiment of the present invention, syringe 94 is suitably configured to operate in a conventional matter and deliver injectable fluid 96 into a bone region (not shown) via delivery through adapter 80A and screw 30. As previously briefly mentioned above, in accordance with one aspect of the current invention, a delivery aid may be utilized in the delivery of fluid (e.g., cement) to the distal most regions of screw 30. As shown in FIGS. 15 and 15A, a delivery aid in the form of an extender tip 98 may be suitably provided to communicate with adapter 80A and syringe 94 so as to provide an extended delivery path for injectable fluid 96 within screw 30.

Although not shown in connection with any of the various figures, in addition to or as an alternative to use of fluid delivery aid 98, capping pins may be utilized to deliver (e.g., by pushing) cement or other injectable fluids through slots and/or holes located about the length of the devices in accordance with the invention described herein.

As previously briefly referred to hereinabove, the various devices in accordance with the present invention may be suitably utilized in connection with the delivery of medicants, bone growth stimulators and/or other fluids. Given the particular configuration as has now been described, those skilled in the art will likely recognize that use of the devices disclosed herein may offer significant advantages over present delivery devices. For example, in treatment of a manastisized region of a bone, a device, in the form of device 30 may be utilized to aid in the delivery, even on a repeated basis, of medicants or other fluids to the manastisized region. Alternatively, a device in accordance with the present invention, for example screw 30, may be implanted within a bone in proximity to the manastisized region and a introduction aid, such as tubing or the like, can be attached to the head thereof to facilitate external delivery of such medicants to the region of interest. In certain applications utilizing the devices in accordance with the present invention for the delivery of fluids to a bone region of interest it may be desirable to use conventional capping pins or other devices to, in effect, block the cannula (e.g., inner bore) of the screws disclosed herein after introduction of the injectable fluid.

Figure 16:
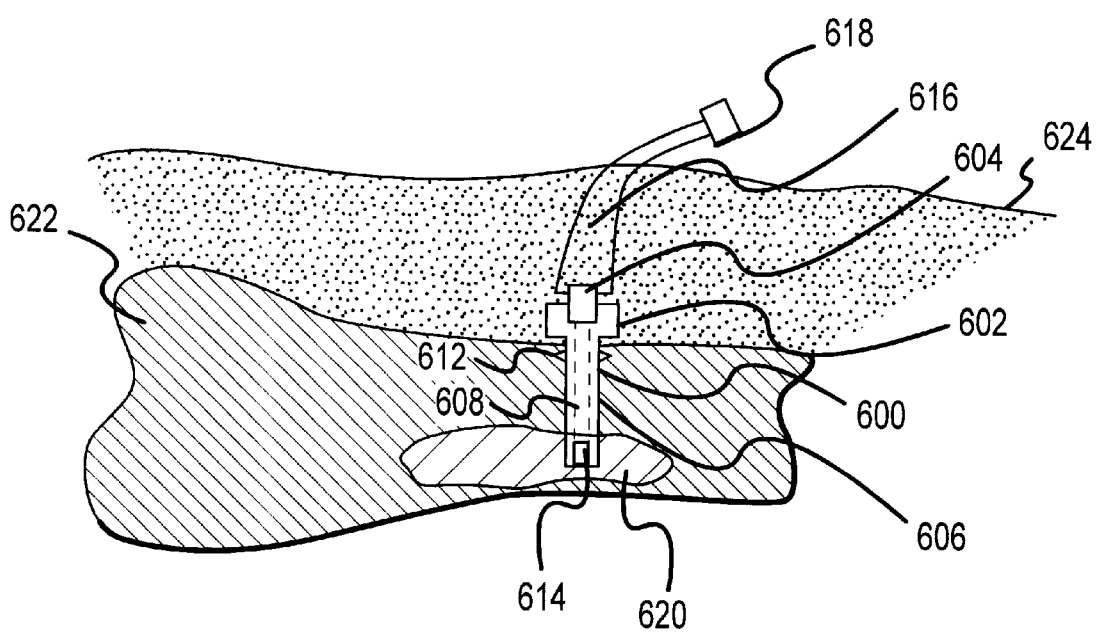
FIG. 16 is a cross-sectional view of a delivery device in accordance with the present invention together with an adapter useful in the delivery of medicants to a region of interest.

For example, with reference now to FIG. 16 a device 600, preferably in the form of a nail, may be inserted into a bone 622 lying underneath the skin 624 of a patient. As shown, screw 600 is suitably configured for insertion into the bone such that its distal end comes in contact with a tumorous region 620. As will be explained, through use of the nail 600, medicants may be delivered to region 620 to aid in treatment thereof. Screw 600 preferably includes a head 602, a shaft 606 with a central cannula 608 spanning therealong. A slot 614 is provided in the distal end of shaft 606 which slot 614 suitably communicates with cannula 608. Head 602 is suitably configured for receipt of an attachment mechanism 604 which is suitably used to secure attachment of a delivery tube 616. As shown, delivery tube 616 suitably extends from adaptor 604 through the skin 624 to provide for an external insertion point 618. Adaptor 618 is suitably configured for receipt of a medicant delivery device. In the context of this embodiment of the present invention, nail 600 may be provided with suitable notches or protrusion 612 to aid in securing nail 600 to bone 622.

Although the present invention has been described in conjunction with particular embodiments illustrated in the appended drawing figures, various modifications may be made without departing from the spirit and scope of the invention as set forth in the appended claims. For example, the design and arrangement of the elements may be modified for particular applications, additional applications may be developed and/or methods utilized in view of the disclosures provided herein.

We claim:

1. A device for forming fixation masses about a portion of a bone consisting of:
   a head portion having an injection site for releasably attaching an injection device to said injection site;
   a threaded shaft portion having a proximal portion and a distal portion, said shaft portion terminating at a tip portion;
   a cannula extending along at least a portion of a length of said shaft portion from said injection site on said head portion substantially along a center-line within said shaft portion, said cannula configured to receive a fixation substance; and
   at least one slot in said proximal portion and at least one slot in said distal portion, said slots in fluid communication with the cannula for delivery of said fixation substance about said device and in proximity to a cortex portion of the bone.

2. The device in accordance with claim 1, wherein said at least one slot is disposed proximate said head portion and said at least one slot is disposed proximate said tip portion.

3. The device in accordance with claim 2, wherein said cannula has a cross sectional area and each of said slots has a cross sectional area, the cross sectional area of said cannula less than the cross-sectional area of each of said slots.

4. The device in accordance with claim 1, wherein said cannula extends from said injection site on said head portion through said shaft portion and through said tip portion for delivery of said hardening substance to strengthen the fixation about an outer cortex portion of the bone.

5. The device in accordance with claim 1, wherein said head portion comprises means for engaging and turning said device for insertion and slot alignment into the bone.

6. The device in accordance with claim 1, wherein said head portion further includes an indicator to indicate the orientation of at least one of said at least one slot.

7. A bone anchoring system comprising:
   a bone anchoring device; including
   a head portion at a proximal end of said anchoring device, the head portion having an attachment means for attaching an injection device and an engagement means for engaging with a tool for inserting said anchoring device;
   an elongate shaft portion having an external threaded portion and a cannula extending along at least a portion of the shaft portion, said cannula suitably configured to internally deliver an anchoring substance;
   a tip portion at a distal end of shaft portion; and
   at least one delivery at said proximal end and at least one delivery port at said distal end, said delivery ports extending from said cannula to deliver said anchoring substance near a bone surface and to form an anchoring mass about said anchoring device and the bone, and a bone plate engaged with said head portion of said bone anchoring device, said bone plate having a surface for at least partial contact with the bone.

8. The bone anchoring system in accordance with claim 7, wherein said attachment means comprises a recess formed in said head portion, said recess threaded for engagement with an injection device.

9. The bone anchoring system in accordance with claim 7, further comprising a coupling assembly for attaching a fixation device to said head portion of said anchoring device.

10. The bone anchoring system in accordance with claim 7, wherein said tip portion comprises an opening in fluid communication with said cannula to deliver said anchoring substance near the bone surface.

11. The bone anchoring system in accordance with claim 7, comprising a plurality of delivery ports located along said shaft portion and extending from said cannula, for delivery of said anchoring substance to maintain optimum anchoring strength of the device.

12. The bone anchoring system in accordance with claim 7, wherein said head portion further includes an adapter device for forcing said anchoring substance through said cannula and out of said port.

13. The bone anchoring system in accordance with claim 7, where said screw further includes a plug for sealing said cannula after insertion of an injectable material therein.

14. A method for strengthening fixation of a fixation device to a bone comprising the steps of:
   (a) providing a fixation device;
   (b) drilling a pilot hole in the bone;
   (c) inserting said fixation device into said pilot hole;
   (d) injecting a fixation substance into a cannula of said fixation device;
   (e) delivering said fixation substance about the bone through a plurality of slots extending outward from said cannula;
   (f) forming areas of fixation masses near at least one of a proximal portion and a distal portion of said fixation device and the bone.

15. The method of claim 14 wherein said providing a fixation device step comprises at least one of or a combination thereof a bone screw, a plate, a pin, a wire, a rod or a nail.

16. The method of claim 14 wherein said providing step comprises pretreating said fixation device with a bone-growth agent.

17. The method of claim 14 further comprising the step of positioning said slots near a cortex portion of the bone.

18. The method of claim 17 wherein the step of positioning comprises a first slot positioned near an endosteum of a cortex portion of the bone and a second slot positioned near a periosteum of a cortex portion of the bone.

19. The method of claim 14 wherein the step of delivering comprises delivering said fixation substance in proximity to a cortex of the bone.

20. The method of claim 14 further comprising the steps of:
   (a) attaching a delivery device comprising said fixation substance to a head of said fixation device prior to said injection step; and
   (b) detaching said delivery device from said head of said fixation device after said delivering step.

21. A method of forming an anchor for an internal fixation device in a vertebral body comprising the steps of:
   (a) inserting at least one fixation device into the vertebral body, said fixation device having a cannula and at least one slot extending outward from said cannula; and
   (b) delivering through said slot an anchoring substance to form a mass about said fixation device and in proximity to an outermost region of a centrum area of the vertebral body.

22. The method of claim 21 further comprising the steps of:
   (a) attaching a fixation component to a head of said fixation device; and
   (b) aligning said fixation component and said fixation device for optimum support in the vertebral body.

23. The method of claim 21 further comprising the step of injecting said anchoring substance into a cannula of said fixation device.

24. The method of claim 21 further comprising the step of prefilling said fixation device with said anchoring substance prior to said inserting step.

25. The device in accordance with claim 1 comprising two slots, a first slot disposed proximate said head portion for delivery of said fixation substance to strengthen an uppermost inner cortex portion of the bone, and a second slot disposed proximate said tip portion for delivery of said fixation substance to strengthen a lowermost inner cortex portion of the bone, and wherein said cannula extends from said injection site on said head portion through said shaft portion and through said tip portion for delivery of said fixation substance to strengthen an outer cortex portion of the bone.

26. A method for increasing the holding power of a bone fixation device comprising the steps of:

(a) engaging said device within the bone;

(b) disposing a bone cement through a bore in said device and through at least two openings in said device;

(c) disbursing said cement through a first opening proximate to a head portion of said device near an inner cortex portion of the bone, and through a second opening proximate to a tip potion of said device near an outer cortex portion of the bone; and (d) curing said cement to form a cement mass about said device and the bone.

27. The method of claim 26, wherein said engaging step comprises predrilling a pilot hole and inserting into said pilot hole.

28. The method of claim 26, wherein said disposing step comprises disposing said cement through three opening in said device, and said disbursing step comprises disbursing through a first opening proximate to a head portion of said device near an upper inner cortex portion of the bone, and disbursing through a second opening proximate to a tip portion of said device near a lower inner cortex portion of the bone, and disbursing through a third opening proximate said tip portion near a lower outer cortex portion of the bone.

29. The method of claim 26, wherein said engaging step comprises placing a bone plate atop the bone and inserting at least one bone screw through said bone plate into the bone.

30. The device in accordance with claim 6, wherein said fixation substance forms a fixation mass about a portion of the bone in compliance with an orientation of said slot.

31. The device in accordance with claim 30, wherein said orientation of said slot is optimized to strengthen the fixation of said device about the bone.

32. The device in accordance with claim 1, wherein said first slot delivers said fixation substance to form a fixation mass to strengthen the fixation about an inner cortex portion of the bone.

33. The device in accordance with claim 1, wherein said fixation substance comprises a hardening substance.

34. The device in accordance with claim 33, wherein said fixation substance comprises bone cement.

\* \* \* \* \*

/

(12) EX PARTE REEXAMINATION CERTIFICATE (9912th)
United States Patent
Karpman et al.

(10) Number: US 6,214,012 C1
(45) Certificate Issued: Oct. 28, 2013

(54) METHOD AND APPARATUS FOR DELIVERING MATERIAL TO A DESIRED LOCATION

(75) Inventors: Robert R. Karpman, Phoenix, AZ (US); Thomas M. Hansen, Phoenix, AZ (US); Anna G. U. Brantley, Tempe, AZ (US)

(73) Assignee: Stryker Spine, Cestas (FR)

Reexamination Request:
No. 90/012,168, Apr. 29, 2012

Reexamination Certificate for:
Patent No.: 6,214,012
Issued: Apr. 10, 2001
Appl. No.: 09/191,915
Filed: Nov. 13, 1998

(51) Int. Cl.
*A61B 17/86* (2006.01)
*A61B 17/88* (2006.01)
*A61B 17/68* (2006.01)
*A61B 17/80* (2006.01)
*A61B 17/70* (2006.01)
*A61F 2/46* (2006.01)

(52) U.S. Cl.
USPC ............ 606/93; 606/246; 606/304; 606/312; 606/71; 606/92

(58) Field of Classification Search
USPC ..................................... 606/65, 304
See application file for complete search history.

(56) References Cited

To view the complete listing of prior art documents cited during the proceeding for Reexamination Control Number 90/012,168, please refer to the USPTO's public Patent Application Information Retrieval (PAIR) system under the Display References tab.

*Primary Examiner* — David O. Reip

(57) ABSTRACT

A method and apparatus for the effective delivery of a material, such as cement, to a desired location in a human. In one embodiment of the invention, a bone screw, including a head portion, a cannulated slotted shaft portion and a tip portion, includes an injection site for removably attaching an injection device, such as a syringe. Since the shaft portion is slotted, injected material flows from the cannulated shaft and is able to exit into surrounding tissue through the slot in the shaft.

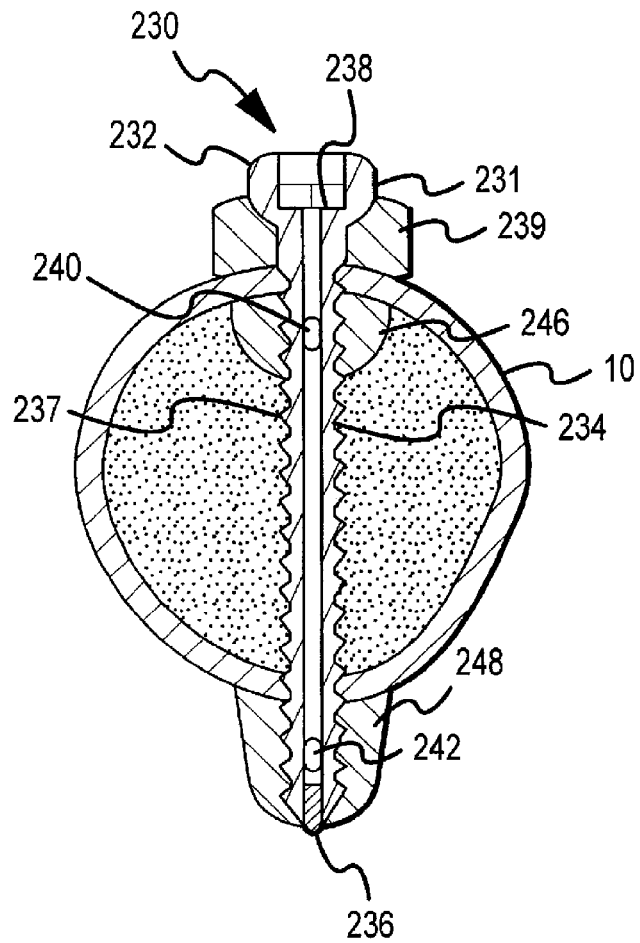

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1, 2, 4, 5, 7-11, 14, 15, 17, 19-23, 25-27, 29 and 32-34 are cancelled.

Claims 3, 6, 12, 13, 16, 18, 24, 28, 30 and 31 were not reexamined.

* * * * *